(12) United States Patent
Libera (10) Patent No.: US 8,093,039 B2
(45) Date of Patent: Jan. 10, 2012

(54) SURFACES DIFFERENTIALLY ADHESIVE TO EUKARYOTIC CELLS AND NON-EUKARYOTIC CELLS

(75) Inventor: Matthew R. Libera, New Providence, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 946 days.

(21) Appl. No.: 12/082,024

(22) Filed: Apr. 8, 2008

(65) Prior Publication Data

US 2008/0255677 A1  Oct. 16, 2008

Related U.S. Application Data

(60) Provisional application No. 60/922,720, filed on Apr. 10, 2007.

(51) Int. Cl.
  *C12M 1/00* (2006.01)
  *A61F 2/00* (2006.01)
  *C12N 11/08* (2006.01)
  *C12N 5/00* (2006.01)
  *C12N 5/07* (2006.01)
  *C07K 17/08* (2006.01)

(52) U.S. Cl. ............ 435/283.1; 424/423; 435/180; 435/395; 435/396; 435/397; 435/402; 530/815

(58) Field of Classification Search .............. None
  See application file for complete search history.

(56) References Cited

U.S. PATENT DOCUMENTS

| | | |
|---|---|---|
| 3,470,078 A | 9/1969 | King |
| 4,652,470 A | 3/1987 | Das et al. |
| 4,684,558 A | 8/1987 | Keusch et al. |
| 4,997,656 A | 3/1991 | Shikinami et al. |
| 5,143,071 A | 9/1992 | Keusch et al. |
| 5,171,264 A | 12/1992 | Merrill |
| 5,212,273 A | 5/1993 | Das et al. |
| 5,219,325 A | 6/1993 | Hennink et al. |
| 5,275,838 A | 1/1994 | Merrill |
| 5,354,790 A | 10/1994 | Keusch et al. |
| 5,480,717 A | 1/1996 | Kundel |
| 5,505,957 A | 4/1996 | D'Angelo et al. |
| 5,567,435 A | 10/1996 | Hubbell et al. |
| 5,593,395 A | 1/1997 | Martz |
| 5,624,711 A * | 4/1997 | Sundberg et al. ............ 506/32 |
| 5,626,863 A | 5/1997 | Hubbell et al. |
| 5,650,165 A | 7/1997 | Akemi et al. |
| 5,674,275 A | 10/1997 | Tang et al. |
| 5,674,346 A | 10/1997 | Kundel |
| 5,700,585 A | 12/1997 | Lee |
| 5,712,346 A | 1/1998 | Lee |
| 5,755,788 A | 5/1998 | Strauss |
| 5,807,636 A | 9/1998 | Sheu et al. |
| 5,837,377 A | 11/1998 | Sheu et al. |
| 5,840,329 A | 11/1998 | Bai |
| 5,846,214 A | 12/1998 | Makuuchi et al. |
| 5,863,201 A | 1/1999 | Lazzara et al. |
| 5,894,799 A | 4/1999 | Bart et al. |
| 5,916,585 A | 6/1999 | Cook et al. |
| 5,952,232 A | 9/1999 | Rothman |
| 6,068,053 A | 5/2000 | Shaw |
| 6,068,853 A | 5/2000 | Giannos et al. |
| 6,103,785 A | 8/2000 | Kajikawa et al. |
| 6,132,765 A | 10/2000 | DiCosmo et al. |
| 6,187,872 B1 | 2/2001 | Yanase et al. |
| 6,228,390 B1 | 5/2001 | Kundel |
| 6,231,970 B1 | 5/2001 | Andersen et al. |
| 6,306,422 B1 | 10/2001 | Batich et al. |
| 6,306,922 B1 | 10/2001 | Hubbell et al. |
| 6,316,018 B1 | 11/2001 | Ding et al. |
| 6,326,149 B1 * | 12/2001 | Loewy et al. ............ 435/6.11 |
| 6,399,700 B2 * | 6/2002 | Mayes et al. ............ 524/731 |
| 6,444,744 B1 | 9/2002 | Fujimaru et al. |
| 6,468,383 B2 | 10/2002 | Kundel |
| 6,475,808 B1 | 11/2002 | Wagner |
| 6,475,809 B1 | 11/2002 | Wagner et al. |
| 6,488,832 B2 | 12/2002 | Heller |
| 6,497,729 B1 | 12/2002 | Moussy et al. |
| 6,509,098 B1 | 1/2003 | Merrill et al. |
| 6,740,409 B1 | 5/2004 | Granick et al. |
| 6,743,521 B2 | 6/2004 | Hubbell et al. |
| 6,772,642 B2 | 8/2004 | Hajduk et al. |
| 6,783,838 B2 | 8/2004 | Coleman et al. |
| 6,806,028 B2 | 10/2004 | Kubota |
| 6,821,762 B2 * | 11/2004 | Stroh et al. ............ 435/174 |

(Continued)

FOREIGN PATENT DOCUMENTS

| | | |
|---|---|---|
| EP | 1 116 516 | 7/2001 |
| WO | WO 96/30409 | 10/1996 |
| WO | WO 00/04389 | 1/2000 |
| WO | WO 02/17888 | 3/2002 |

OTHER PUBLICATIONS

Hong Ye, et al., Protein Surface Patterning Using Nanoscale PEG Hydrogels, Langmuir, Aug. 13, 2004, pp. A-D.
Constans, Aileen, The Chipping News, Protein Arrays and Biochips Speed Up Protein Functional Analysis and Expression Profiling, The Scientist, Apr. 29, 2002, pp. 28-30.

(Continued)

*Primary Examiner* — David Naff
(74) *Attorney, Agent, or Firm* — Greenberg Traurig, LLP (57) ABSTRACT

A surface coating comprises a primer coat that permits adhesion of eukaryotic cells thereto, and a plurality of macromolecular structures attached to the primer coat. At least some of the macromolecular structures have a cell-resistant character, meaning that cells generally will not adhere to them. The macromolecular structures are distributed across an area of the primer coat so that the surface coating permits adhesion of the eukaryotic cells to the primer layer and resists the adhesion of non-eukaryotic cells. Typically, the primer coat comprises a self-assembled polymeric monolayer and the macromolecular structures comprise nanoscale hydrogels. Such surface coatings may be formed on articles of manufacture for insertion into the body, such as orthopedic devices.

13 Claims, 6 Drawing Sheets

U.S. PATENT DOCUMENTS

| | | | |
|---|---|---|---|
| 6,828,096 B1 | 12/2004 | Boussie et al. | |
| 6,884,628 B2* | 4/2005 | Hubbell et al. | 436/518 |
| 6,887,270 B2 | 5/2005 | Miller et al. | |
| 6,905,738 B2 | 6/2005 | Ringeisen et al. | |
| 6,969,400 B2 | 11/2005 | Rhee et al. | |
| 7,033,603 B2 | 4/2006 | Nelson et al. | |
| 7,143,709 B2 | 12/2006 | Brennan et al. | |
| 7,211,209 B2* | 5/2007 | Kim et al. | 264/129 |
| 7,361,724 B2 | 4/2008 | Guire et al. | |
| 7,763,423 B2* | 7/2010 | Roitman et al. | 435/6.11 |
| 7,908,908 B2* | 3/2011 | Brown et al. | 73/105 |
| 2001/0041349 A1 | 11/2001 | Patron et al. | |
| 2002/0007217 A1 | 1/2002 | Jacob et al. | |
| 2002/0010261 A1 | 1/2002 | Callahan et al. | |
| 2002/0037383 A1 | 3/2002 | Spillman, Jr. et al. | |
| 2002/0071902 A1 | 6/2002 | Ding et al. | |
| 2002/0091229 A1 | 7/2002 | Hubbell et al. | |
| 2002/0106702 A1 | 8/2002 | Wagner et al. | |
| 2002/0110932 A1 | 8/2002 | Wagner et al. | |
| 2002/0110933 A1 | 8/2002 | Wagner et al. | |
| 2002/0119579 A1 | 8/2002 | Wagner | |
| 2002/0132272 A1 | 9/2002 | Wagner et al. | |
| 2002/0182633 A1 | 12/2002 | Chen et al. | |
| 2003/0031699 A1 | 2/2003 | Van Antwerp et al. | |
| 2003/0054024 A1 | 3/2003 | Munro et al. | |
| 2003/0069383 A1 | 4/2003 | Van Antwerp et al. | |
| 2003/0077447 A1 | 4/2003 | Senak | |
| 2003/0082225 A1 | 5/2003 | Mason | |
| 2003/0087099 A1 | 5/2003 | Merrill et al. | |
| 2003/0157260 A1 | 8/2003 | Rubner et al. | |
| 2004/0028655 A1 | 2/2004 | Nelson et al. | |
| 2004/0137039 A1 | 7/2004 | Sukhishvili et al. | |
| 2005/0003146 A1 | 1/2005 | Spath | |
| 2005/0008828 A1 | 1/2005 | Libera et al. | |
| 2005/0167261 A1 | 8/2005 | Deutchman et al. | |
| 2005/0191430 A1 | 9/2005 | Rubner et al. | |
| 2005/0221072 A1 | 10/2005 | Dubrow et al. | |
| 2005/0228491 A1 | 10/2005 | Snyder et al. | |
| 2006/0014003 A1 | 1/2006 | Libera et al. | |
| 2006/0204738 A1 | 9/2006 | Dubrow et al. | |
| 2006/0219143 A1 | 10/2006 | Brennan et al. | |
| 2007/0225823 A1 | 9/2007 | Hawkins et al. | |
| 2007/0259427 A1 | 11/2007 | Storey et al. | |
| 2007/0286883 A1 | 12/2007 | Lensen et al. | |

OTHER PUBLICATIONS

MacBeath, Gavin, et al., Printing Proteins as Microarrays for High-Throughput Function Determination, Science, Sep. 8, 2000, pp. 1760-1763, vol. 289.

Tan, John L., et al., Microcontact Printing of Proteins on Mixed Self-Assembled Monolayers, Langmuir, 2002, pp. 519-523, vol. 18.

Templin, Markus F., et al., Protein Microarray Technology, Trends in Biotechnology, Apr. 4, 2002, pp. 160-166, vol. 20, No. 4.

Yadavalli, Vamsi K., Microfabricated Protein-Containing Poly(ethylene glycol) Hydrogel Arrays for Biosensing, Sensors and Actuators, 2004, pp. 290-297, vol. 97.

Michel, B., et al., Printing Meets Lithography: Soft Approaches to High-Resolution Patterning, IBM J. Res. & Dev., Sep. 2001, pp. 697-718, vol. 45, No. 5.

Kenseth, Jeremy R., Investigation of Approaches for the Fabrication of Protein Patterns by Scanning Probe Lithography, Langmuir, 2001, pp. 4105-4112, vol. 17.

Lee, Ki-Bum, et al., Protein Nanostructures Formed via Direct-Write Dip-Pen Nanolithography, J. Am. Chem. Soc., 2003, pp. 5588-5589, vol. 125.

Liu, Gang-Yu, et al., Nanofabrication of Self-Assembled Monolayers Using Scanning Probe Lithography, Acc. Chem. Res., 2000, pp. 457-466, vol. 33, No. 7.

Wadu-Mesthrige, Kapila, et al., Fabrication and Imaging of Nanometer-Sized Protein Patterns, Langmuir, 1999, pp. 8580-8583, vol. 15.

Bergman, Anna A., Nanometer-Scale Arrangement of Human Serum Albumin by Adsorption on Defect Arrays Created with a Finely Focused Ion Beam, Langmuir, 1998, pp. 6785-6788, vol. 14.

Mendes, Paula M., et al., Gold Nanoparticle Patterning of Silicon Wafers Using Chemical e-Beam Lithography, Langmuir, 2004, pp. 3766-3768, vol. 20.

Stamou, D., et al., Site-Directed Molecular Assembly on Templates Structured with Electron-Beam Lithography, Langmuir, 2004, pp. 3495-3497, vol. 20.

Revzin, Alexander, et al., Surface Engineering with Poly(ethylene glycol) Photolithography to Create High-Density Cell Arrays on Glass, Langmuir, 2003, pp. 9855-9862, vol. 19.

Sofia, J. Susan, et al., Poly(ethylene glycol) Grafted to Silicon Surfaces: Grafting Density and Protein Adsorption, Macromolecules, 1998, pp. 5059-5070, No. 31.

Prime, Kevin L., et al., Adsorption of Proteins onto Surfaces Containing End-Attached Oligo (ethylene oxide): A Model System Using Self-Assembled Monolayers, J. Am. Chem. Soc., 1993, pp. 10714-10721, No. 115.

Gombotz, Wayne R., et al., Protein Adsorption to Poly(ethylene oxide) Surfaces, J. Biomed. Mater. Res., 1991, pp. 1547-1562, vol. 25.

Alcantar, Norma A., et al., Polyethylene Glycol-coated Biocompatible Surfaces, J. Biomed Mater. Res., 2000, pp. 343-351, vol. 51.

Kao, Weiyuan John, et al., Murine Macrophage Behavior on Peptide-Grafted Polyethyleneglycol-Containing Networks, Biotechnol. Bioeng., 1998, pp. 2-9, vol. 59.

Kao, Weiyuan John, Evaluation of Protein-Modulated Macrophage Behavior on Biomaterials: Designing Biomimetic Materials for Cellular Engineering, Biomaterials, 1999, pp. 2213-2221, vol. 20.

Gobin, Andrea S., et al., Effects of Epidermal Growth Factor on Fibroblast Migration through Biomimetic Hydrogels, Biotechnol. Prog, 2003, pp. 1781-1785, vol. 19.

Drumheller, Paul D., et al., Polymer Networks with Grafted Cell Adhesion Peptides for Highly Biospecific Cell Adhesive Substrates, Analytical Biochemistry, 1994, pp. 380-388, vol. 222.

Guschin, Dmitry, et al., Manual Manufacturing of Oligonucleotide, DNA, and Protein Microchips, Analytical Biochemistry, 1997, pp. 203-211, vol. 50.

Arenkov, Pavel, et al., Protein Microchips: Use for Immunoassay and Enzymatic Reactions, Analytical Biochemistry, 2000, pp. 123-131, vol. 278.

Krsko, P., et al., Electron-Beam Surface-Patterned Poly(ethylene glycol) Microhydrogels, Langmuir, 2003, pp. 5618-5625, vol. 19.

Hermanson, Greg T., Bioconjugate Techniques, 1996, Sections 3.3-3.5, Academic Press, San Diego.

Murata, Kenji, et al., Monte Carlo Simulation of Fast Secondary Electron Production in Electron Beam Resists, J. Appl. Phys., Jul. 1981, pp. 4396-4405, vol. 52, No. 7.

Thompson, Larry F., et al., Introduction to Microlithography, 1994, pp. 284-291 and 354-355, American Chemical Society, Washington DC.

Siangchaew, K., et al., The Influence of Fast Secondary Electrons on the Aromatic Structure of Polystyrene, Philosophical Magazine A, 2000, pp. 1001-1016, vol. 80, No. 4, Taylor & Francis Ltd, London, UK.

Ito, Yoshihiro, Surface Micropatterning to Regulate Cell Functions, Biomaterials, 1999, pp. 2333-2342, vol. 20.

Kane, Ravi S., et al., Patterning Proteins and Cells Using Soft Lithography, Biomaterials, 1999, pp. 2363-2376, vol. 20.

Chen, Christopher S., et al., Geometric Control of Cell Life and Death, Science, May 30, 1997, pp. 1425-1428, vol. 276.

Hyun, Jinho, et al., Micropatterns of a Cell-Adhesive Peptide on an Amphiphilic Comb Polymer Film, Langmuir, 2002, pp. 2975-2979, vol. 18.

James, C.D., et al., Patterned Protein Layers on Solid Substrates by Thin Stamp Microcontact Printing, Langmuir, 1998, pp. 741-744, vol. 14.

Singhvi, Rahul, et al., Engineering Cell Shape and Function, Science, Apr. 29, 1994, pp. 696-698, vol. 264.

Chiu, Daniel T., et al., Patterned Deposition of Cells and Proteins onto Surfaces by Using Three-Dimensional Microfluidic Systems, Proc. Nat. Acad. Sci. USA, Mar. 14, 2000, pp. 2408-2413, vol. 97, No. 6.

Delamarche, Emmanuel, et al., Microfluidic Networks for Chemical Patterning of Substrates: Design and Application to Bioassays, J. Am. Chem. Soc., 1998, pp. 500-508, vol. 120.

Folch, Albert, et al., Cellular Micropatterns on Biocompatible Materials, Biotechnol. Prog., May 1998, pp. 388-392, vol. 14.

Park, Ann, et al., Integration of Surface Modification and 3D Fabrication Techniques to Prepare Patterned Poly(L-lactide) Substrates Allowing Regionally Selective Cell Adhesion, J. Biomater. Sci. Polymer Edn., 1998, pp. 89-110, vol. 9, No. 2.

Lee, Ki-Bum, et al., Protein Nanoarrays Generated by Dip-Pen Nanolithography, Science, Mar. 1, 2002, pp. 1702-1705, vol. 295.

Nguyen, Kytai Truong, et al., Photopolymerizable Hydrogels for Tissue Engineering Applications, Biomaterials, 2002, pp. 4307-4314, vol. 23.

Peppas, Nicholas A., et al., New Challenges in Biomaterials, Science, Mar. 25, 1994, pp. 1715-1720, vol. 263.

Beebe, David J., et al., Functional Hydrogel Structures for Autonomous Flow Control Inside Microfluidic Channels, Nature, Apr. 6, 2000, pp. 588-590, vol. 404.

Harris, J. Milton, Introduction to Biotechnical and Biomedical Applications of Poly(ethylene glycol), Poly(Ethylene Glycol) Chemistry: Biotechnical and Biomedical Applications, 1992, pp. 1-14, Plenum Press, New York City.

Israelachvili, Jacob, The Different Faces of Poly(Ethylene Glycol), Proc. Natl. Acad. Sci. USA, Aug. 1997, pp. 8378-8379, vol. 94.

Andrade, J. D., et al., Protein Adsorption and Materials Biocompatibility: A Tutorial Review and Suggested Hypotheses, Advances in Polymer Science, 1986, pp. 1-63, vol. 79, Springer-Verlag, Berlin.

Graham, N.B., Poly(Ethylene Glycol) Gels and Drug Delivery, Poly(Ethylene Glycol) Chemistry: Biotechnical and Biomedical Applications, 1992, pp. 263-281, Plenum Press, New York.

Andreopoulos, Fotios M., et al., Light-Induced Tailoring of PEG-Hydrogel Properties, Biomaterials, 1998, pp. 1343-1352, vol. 19.

Cruise, Gregory M., et al., Characterization of Permeability and Network Structure of Interfacially Photopolymerized Poly(ethylene glycol) Diacrylate Hydrogels, Biomaterials, 1998, pp. 1287-1294, vol. 19.

Lu, Sanxiu, et al., Release Behavior of High Molecular Weight Solutes from Poly(ethylene glycol)-Based Degradable Networks, Macromolecules, 2000, pp. 2509-2515, vol. 33.

Mellott, Michael B., et al., Release of Protein from Highly Cross-Linked Hydrogels of Poly(ethylene glycol) Diacrylate Fabricated by UV Polymerization, Biomaterials, 2001, pp. 929-941, vol. 22.

Kofinas, Peter, et al., Hydrogels Prepared by Electron Irradiation of Poly(Ethylene Glycol) in Water Solution: Unexpected Dependence of Cross-Link Density and Protein Diffusion Coefficients on Initial PEO Molecular Weight, Biomaterials, 1996, pp. 1547-1550, vol. 17.

Rosiak, J.M., et al., Synthesis of Hydrogels by Irradiation of Polymers in Aqueous Solution, Radiation Physics and Chemistry, 1999, pp. 139-151, vol. 55.

Sofia, Susan J., et al., Grafting of PEO to Polymer Surfaces Using Electron Beam Irradiation, J. Biomed. Mater. Res., 1998, pp. 153-163, vol. 40.

Flory, Paul J., Principles of Polymer Chemistry, 1953, pp. 576-594, Cornell University Press, Ithaca, New York.

Merrill, Edward W., et al., Partitioning and Diffusion of Solutes in Hydrogels of Poly(ethylene oxide), Biomaterials, 1993, pp. 1117-1126, vol. 14, No. 15.

Zhang, Lihua, et al., Radiation Effects on Crystalline Polymers—I. Gamma-Radiation-Induced Crosslinking and Structural Characterization of Polyethylene Oxide, Radiat. Phys. Chem., 1992, pp. 501-505, vol. 40, No. 6.

Rai-Choudhury, P., Electron Beam Lithography, Handbook of Microlithography, Micromachining, and Microfabrication: vol. 1: Microlithography, 1997, pp. 160-169, SPIE Optical Engineering Press, Bellingham, Washington.

Kurtz, Steven M., et al., Advances in the Processing, Sterilization and Crosslinking of Ultra-High Molecular Weight Polyethylene for Total Joint Arthroplasty, Biomaterials, 1999, pp. 1659-1688, vol. 20.

Ditchfield, R.W., et al., Electron Energy Loss Studies of Polymers During Radiation Damage, Philosophical Magazine, 1973, pp. 1267-1280, vol. 27, No. 6, Taylor & Francis Ltd, London, UK.

Merrill, Edward W,. et al., Polyethylene Oxide As a Biomaterial, Journal of the American Society for Artificial Internal Organs, 1983, pp. 60-64, vol. 6.

Goodberlet, James G., et al., Performance of the Raith 150 Electron-Beam Lithography System, J. Vac. Sci. Technol. B, Nov./Dec. 2001, pp. 2499-2503, vol. B19, No. 6, Taylor & Francis Ltd, London, UK.

Ingber, Donald E., Fibronectin Controls Capillary Endothelial Cell Growth by Modulating Cell Shape, Pro. Natl. Acad. Sci USA., May 1990, pp. 3579-3583, vol. 87.

Quake, Steven R., et al., From Micro to Nanofabrication with Soft Materials, Science, Nov. 24, 2000, pp. 1536-1540, vol. 290.

Office Action, dated Jan. 30, 2006, received in U.S. Appl. 10/626,472, filed Jul. 24, 2003.

Amendment dated May 30, 2006, in response to Office Action dated Jan. 30, 2006, received in U.S. Appl. No. 10/626,472, filed Jul. 24, 2003.

Office Action, dated Sep. 27, 2006, received in U.S. Appl. No. 10/626,472, filed Jul. 24, 2003.

Office Action, dated Dec. 10, 2007, received in U.S. Appl. No. 11/141,339, filed May 31, 2005.

Guangsheng Guo, et al. "Preparation of Hydroxyapatite Nanoparticles by Reverse Microemulsion," Ceramics International 31 (2005) pp. 869-872.

Douglas B. Weibel, et al. "Microfabrication Meets Microbiology," Nature Reviews Microbiology. vol. 5, Mar. 2007, pp. 209-218.

* cited by examiner

SURFACES DIFFERENTIALLY ADHESIVE TO EUKARYOTIC CELLS AND NON-EUKARYOTIC CELLS

CROSS-REFERENCE TO RELATED APPLICATIONS

The present application claims benefit of U.S. Provisional Patent Application No. 60/922,720, filed on Apr. 10, 2007, the disclosure of which is incorporated herein by reference, in its entirety.

FIELD OF THE INVENTION

This invention is related to the field of surface coatings, particularly those having cell-resistant properties. It is also related to the field of biomedical devices, particularly those, such as orthopedic devices, that are intended for implantation in the human body.

BACKGROUND OF THE INVENTION

Surfaces have been extensively modified by chemical, biochemical, and topographic means to render them either adhesive or resistant to cells, and the resulting knowledge base has had a very substantial impact both on the basic scientific understanding of cell-material interactions as well as on important applications associated with biomedical devices and tissue-engineering constructs. Because of the many varied specific and non-specific mechanisms involved in cell adhesion, however, a surface that is adhesive to one cell type is usually also adhesive, to varying degrees, to other cell types. The surfaces of orthopedic implants are no exception. The oxidized metal or hydroxyapatite-coated surfaces used in most implant applications satisfy the critical design criteria of being osteoinductive, but they are also adhesive to bacteria. A number of materials modifications have been made to render such surfaces resistant to bacteria—PEGylation, for example, has been used—but these bacteria-resistant surfaces also resist adhesion of eukaryotic cells.

Surface coatings having submicron features offer a solution to the problem of creating a surface that is differentially adhesive to osteoblasts and bacteria. This solution is based on the modulation of surface adhesiveness using nanoscale hetero-features organized on surfaces in two dimensions at sub-micron length scales. Such patterning is being explored in several contexts, including control of cell adhesiveness. However, the idea of modulating nanoscale adhesiveness to achieve differential cell adhesion based on fundamental differences in the length-scale properties of bacteria and eukaryotic cells is new.

SUMMARY OF THE INVENTION

This invention provides a new surface treatment that permits the adhesion of one or more types of eukaryotic cells on a surface while simultaneously resisting adhesion by one or more types of non-eukaryotic cells (e.g., bacteria). This differential adhesiveness has applicability toward reducing the risk of infection associated with articles to be implanted in living bodies.

In one embodiment, the invention provides a surface coating that is differentially adhesive to bacteria and eukaryotic cells, and comprises a primer coat that permits eukaryotic cells to adhere thereto, and a plurality of macromolecular structures, such as nanohydrogels, attached to the primer coat. At least some of the macromolecular structures are cell-resistant (i.e., they resist the adhesion of cells thereto), and are sufficiently distributed across an area of the primer coat so as to permit the adhesion of eukaryotic cells thereto, and repel bacteria therefrom.

In another embodiment, the primer coat of the surface coating described above, is provided with a factor to promote the adhesion of eukaryotic cells to the primer coat.

In yet another embodiment, the surface coating is provided with both cell-resistant macromolecular structures and macromolecular structures that include a factor to promote the adhesion of eukaryotic cells thereto.

In a further embodiment, the primer coat comprises a self-assembled monolayer of polymer formed by electrostatic self-assembly of the monolayer on a substrate, and the macromolecular structures are deposited on the primer coat by electrostatic self-assembly on the monolayer.

In a yet further embodiment, an article is provided having the surface coating assembled upon it, and, in a variation of the yet further embodiment, the surface coating is self-assembled on a continuous, topographically complex surface of the article.

DETAILED DESCRIPTION OF THE INVENTION

For the purposes of the present disclosure, the following definitions are to be applied:

A macromolecular structure is any particle having submicron lengths along at least two dimensions, preferably in the range of about 50 nm to about 250 nm, and having a cell-resistant or cell-adhesive macromolecule, preferably a gel, exposed at a surface thereof. A nanohydrogel is an example of a macromolecular structure.

A hydrogel is a type of gel (i.e., an intramolecularly cross-linked macromolecule that can swell in the presence of a solvent) that specifically interacts with water and water-based solutions, including physiological media. It may be noted that both cell-resistant and cell-adhesive hydrogels are known, and can be formed by appropriate selection of the polymer used, and the degree of cross-linking present.

A nanohydrogel is a hydrogel whose diameter in the swollen state is less than about one micron and, preferably, whose diameter in the fully-hydrated state is less than about 250 nm.

A material is considered to be cell-resistant if cells, including both eukaryotic cells and bacteria, generally will not form adhesive contacts with a surface of the material. It is known that cells generally will not form adhesive contacts with hydrogels that are formed from any of a number of polymers, including, but not limited to poly(ethylene oxide), certain poly(ethylene oxide) acrylates, and other poly(ethylene glycol) derivatives. Other examples of such materials are known to those of ordinary skill in the art.

A material is cell-adhesive if a cell will form an adhesive contact with a surface of the material. A cell that has adhered to a material will not be removed from that surface by mechanical stress such as that associated with rinsing the material with water or a buffer solution.

A cell-adhesion factor is any chemical entity that promotes or mediates adhesion of a cell to another material. Such factors include, but are not limited to, compounds or fragments of compounds such as antigens, antibodies, or extracellular matrix molecules (e.g., laminin, fibronectin, collagen, integrin, serum albumin, polygalactose, sialic acid, lectin-binding sugars, synthetic oligopeptides, or carbohydrates). Other such chemical entities include compounds having functional groups such as, but not limited to, hydrophobic groups or alkyl groups having charged moieties. Other examples of such entities and moieties are known to those of ordinary skill in the art, as well as methods of modifying various materials to include such entities or moieties.

Specific adhesion is adhesion that is mediated by reversible bonds between specific, complementary molecules including, but not limited to: antibodies, or fragments of antibodies, and their antigens, cell surface receptors and their ligands, or lectins and carbohydrates. In the present invention, mechanisms that are known to promote specific adhesion among cells may be adapted to promote adhesion between cells and polymeric structures, or between polymeric structures, by linking the complementary molecules to the polymers. Other examples of such molecules are known to those of ordinary skill in the art.

Non-specific adhesion includes mechanisms of adhesion such as electrostatic attraction, hydrogen bonding, covalent bonding, and other mechanisms of adhesion that do not rely on the reversible bonding between complementary molecules.

A differentially adhesive surface, with respect to cell adhesion, permits the adhesion of one type of cell to the surface, while resisting the adhesion of a different type of cell.

A primer coat comprises one or more layers that are applied to a substrate and form a base to which a macromolecular structure may adhere.

A substrate is considered to be the foundation on which molecules, particularly, but not exclusively, those in the primer layer, may be immobilized.

Electrostatic self-assembly refers to a process by which two different structures, such as, but not limited to, a polymer molecule and a substrate, or a macromolecular structure and a primer coat, attract each other by means of opposite charge or oppositely aligned dipoles, and bind by some form of secondary bonding.

Self-assembled monolayers include, but are not limited to, layers of polymer molecules that adsorb onto a substrate by electrostatic self-assembly. Other methods of forming such self-assembled monolayers are known to those having ordinary skill in the art.

The term "topographically complex" describes surfaces that extend in three dimensions and have been made rough by means such as mechanical abrasion, cutting, or etching, or have been manufactured in such a condition. The term especially applies to the visible and hidden surfaces of articles comprising masses of sintered particles.

The surface coating disclosed herein presents surfaces whose cell adhesiveness is spatially modulated at cellular and subcellular-scale lengths. This spatially modulated adhesiveness provides a mechanism by which such a coating becomes differentially adhesive to different cell types. For example, such a structure has the ability to control the differential adhesion between eukaryotic cells and bacteria because these two classes of cells have characteristic sizes that differ by a factor of 5 to 50, depending upon the specific cell types involved. This ability is not present in surfaces which have been made cell-adhesive by chemical or topographic methods alone, since such surfaces are usually adhesive to many cell types. The surface coating described herein further has direct application to the modification of orthopedic implants, and other objects or devices to be implanted in the human body, where there is a pressing need to preserve the ability of these implants to promote osteointegration via the adhesion and proliferation of osteoblasts (which are a type of eukaryotic cells) while simultaneously reducing the threat of infection by resisting the adhesion of bacteria to the implant. As disclosed herein, the surface coating may be assembled on the surface of such an article by electrostatic self-assembly, enabling the surface coating to be deposited on topographically complex surfaces typical of, for example, modern implants, the surfaces of which are created by masses of sintered beads.

Figure 1:
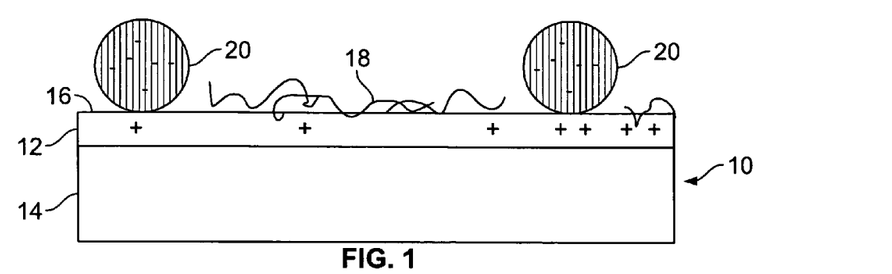
FIG. 1 is a schematic drawing of a surface coating according to a first embodiment of the present invention, comprising cell-resistant macromolecular structures attached to a primer layer laid over a substrate.

FIG. 1 presents a schematic cross-sectional view of one embodiment of a surface coating 10 disclosed herein. In this particular embodiment, a primer coat 12 has been formed on a substrate 14. In this particular example, the primer coat 12 comprises a self-assembled monolayer of a cationic polymer assembled on the substrate 14 by electrostatic deposition. For applications in which the surface coating 10 is to be used in biological applications (e.g., as a coating on a device to be implanted in the human body) the polymer should be able to maintain a positive (+) charge at the surface 16 of the primer coat 12 in physiological media. The primer coat 12 has a cell-adhesive character. The material used to form the primer coat 12 may itself be cell-resistant or cell-adhesive, with the adhesiveness provided or enhanced, respectively, by the addition of one or more cell-adhesion factors 18 to the surface 16 of the primer coat 12. The design of the primer coat 12 is important to the control the structure, heterogeneity, and stability of the self-assembled monolayer of nanohydrogels 20. In the embodiment of FIG. 1, the particular type of nanohydrogels 20 are cell-resistant hydrogels. A suitable polycation primer coat 12 may based on polymers such as poly(L-lysine) (PLL), poly(allylamine hydrochloride) (PAH), or linear/branched polyethyleneimine (PEI), or their copolymers.

It should be noted that the charge and conformation of the polymer in the primer coat 12 plays a significant role in the surface organization of the nanohydrogels 20 deposited upon it. The charge and polymer conformation can be controlled by copolymer composition, pH, and ionic strength, and other properties. It must be practical to controllably deposit the primer coat 12 on both planar (e.g., silicon) and topologically complex (e.g., beaded-metal coupons) substrates in order to mediate subsequent deposition of the nanohydrogels 20. Such substrates typically are coated with oxides of the substrate material, and can maintain a negative (−) charge that will electrostatically attract cationic polymer molecules.

A series of PLL, PAH, or PEI copolymers can be used to give control over the thickness of the primer coat 12 and the molecular conformation of the polymers in the primer coat 12. Importantly, the different adsorption characteristics of different polycation polymers can be used to control surface coverage by the nanohydrogels 20. For example, the thickness of PAH films can be manipulated by varying deposition pH. The fact that the deposited thickness increases with increasing pH reflects the electrostatic nature of interactions between positively-charged PAH segments and the negatively charged substrate. By decreasing pH below the PAH $pK_b$ value of 10.5, the linear charge density of PAH decreases and loopy chain conformations are observed. Such a conformation is important, because it leads to greater deposition of a nanoparticles. Similar control can be achieved by varying the ionic strength during polymer deposition. Polymers adsorbed from low-salt solutions form relatively flat conformations due to the repulsions between charged segments, whereas polymer chains have more loops and tails when adsorbed from high-salt solutions. Analogous arguments can be made concerning the salt and pH-dependent deposition behavior of PEI and PLL.

Spatial modulation of the cell-adhesive properties of the surface coating 10 is provided by cell-resistant macromolecular structures 20 on the surface 16 of the primer coat. In the particular embodiment represented in FIG. 1, the cell-resistant macromolecular structures 20 are cell-resistant nanohydrogels 20 comprising a cross-linked anionic polymer. Similar to the selection of a polymer for the primer coat, selection of the polymer used to synthesize nanohydrogels 20 is important to the structure of the surface coating 10. When a polycationic primer coat 12 is used, the polymer used to synthesize the nanohydrogels 20 should be one that will maintain a negative (−) charge in physiological media (i.e., a polyanionic monomer), while retaining the nanohydrogels' 20 cell-resistant character in such media. The positive (+) charge of the primer coat 12 and the negative (−) charge of the nanohydrogels 20 enable electrostatic self-assembly of the nanohydrogels 20 on the primer coat 12, in an unpatterned lateral distribution across the primer coat 20 (i.e., distributed across two-dimensions). The nanohydrogels 20 adhere to the primer coat 12 by electrostatic attraction and, thus, cannot readily removed from the primer coat 12 by mechanical stress. It may be noted that any type of macromolecular structure 20 may be deposited on a primer coat 12, as long as both the macromolecular structure 20 and primer coat 12 maintain opposite electrical charges, or present oppositely aligned dipoles, in the same media. Further, a macromolecular structure 20 and primer coat 12 may be designed so that they attach to each other by other mechanisms of adhesion, whether specific or non-specific. Such mechanisms can be used to fix the two-dimensional organization of the nanohydrogels 20 after their deposition.

Figure 2:
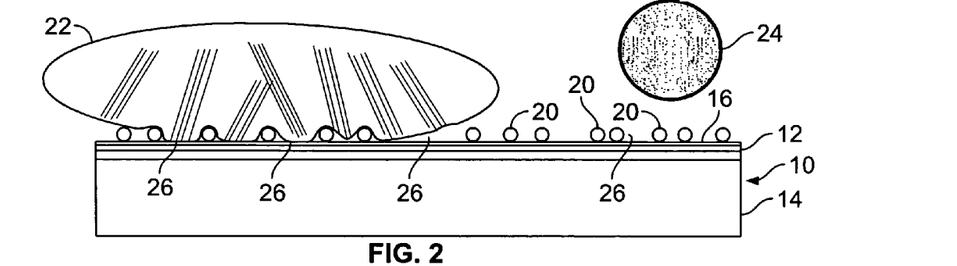
FIG. 2 is a schematic drawing of the surface coating of FIG. 1 in relation to a eukaryotic cell bound thereto and a bacterium.

FIG. 2 presents a schematic cross-sectional view of a larger portion of the surface coating 10 of FIG. 1, illustrating the adhesion of a eukaryotic cell 22, such as an osteoblast, and the absence of adhesion of a bacterium 24, such as a staphylococcal bacterium. Both the size and spacing of the cell-resistant nanohydrogels 20 are important to controlling the differential adhesion of eukaryotic cells 22 and bacteria 24 to the surface coating 10. Significantly, osteoblasts are typically on the order of 5-10 μm in diameter, have flexible cell walls that can conform to a substrate, and adhere to surfaces in the presence of cell-adhesive factors. In contrast to osteoblasts, bacteria such as *Staphylococcus epidermidis* (*S. epi*) and *Staphylococcus aureus* (*S. aureus*) tend to be spherically shaped and do not easily conform to a substrate. In contrast to osteoblasts, staphyloccoci are only about 0.6-0.9 μm in diameter, and their surface adhesion is mediated by both specific and non-specific binding mechanisms. Thus, the cell-resistant nanohydrogels 20 must be spaced such that a bacterium 24 will not have an adequate opportunity to bind to the surface coat 12, while allowing eukaryotic cells 22 to bind to the spaces between the cell-resistant nanohydrogels 20. Accordingly, the cell-resistant nanohydrogels 20, or other macromolecular structures 20 that may be used in their place, should have submicron dimensions (i.e., lengths of less than one micron) in at least two dimensions, and, preferably, have nano-scale dimensions. The cell-resistant nanohydrogels 20 of the embodiment of FIGS. 1 and 2 should have diameters in a preferred range of about 50 nm to about 250 nm. In that size range, the preferred average spacing between the cell-resistant nanohydrogels 20 would be in the range of about 0.2 μm to about 5 μm. Such a spacing would allow the eukaryotic cells 22, with their flexible walls, to adhere to the primer coat 12 within the spaces 26 between the cell-resistant nanohydrogels 20, while bridging such nanohydrogels. The bacteria 24 would be, effectively, repelled from the surface coating 10. The desired differential adhesion of eukaryotic cells 22 relative to bacteria 24 can be achieved when as little as 2-20 percent of the surface area of the primer coat 12 is covered by cell-resistant nanohydrogels 20. However, such differential adhesion can also be achieved when as much as 80-98 percent of the primer coat 12 is so covered. This greater coverage would correspond to a surface coating 10 that is presents an effectively continuous surface that is resistant to bacterial adhesion, but has micron-sized windows for eukaryotic adhesion.

Figure 3:
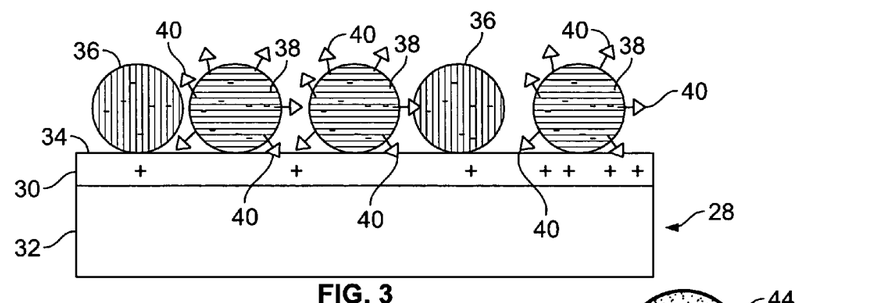
FIG. 3 is a schematic drawing of a surface coating according to a second embodiment of the present invention, comprising cell-resistant and cell-adhesive macromolecular structures attached to a primer layer over a substrate.

FIG. 3 presents a schematic cross-sectional view of a second embodiment of a surface coating 28. In this particular embodiment, a primer coat 30 has been formed on a substrate 32. The primer coat 30 and the substrate 32, as well as the surface 34 of the primer coat 30, may have the same features and characteristics of the respective primer coat 12, substrate 14, and surface 16 of the surface coating 10 of FIGS. 1 and 2, except for the differences that are noted herein. In this second embodiment, the primer coat 30 may be provided with one or more cell-adhesive factors (not shown) exposed at its surface.

At least two types of macromolecular structures 36, 38 are provided at the surface 34 of the primer coat 30. In this second embodiment, the respective macromolecular structures, 36, 38 are cell-repellant nanohydrogels 36 and second family of nanohydrogels (i.e., cell-adhesive nanohydrogels 38), both of which may have the same features and characteristics as the cell-resistant nanohydrogels 20, except for the differences that are noted herein. With respect to the nanohydrogels 36, 38, as well as for macromolecular structures 36, 38 in general, it may be noted that it is not necessary that they be made of the same materials as each other, as long as the materials that are used create nanohydrogels 36, 38 having the desired properties, particularly the ability to maintain a negative (−) charge in physiological media.

The significant difference between the cell-repellant nanohydrogels 36 and the cell-adhesive nanohydrogels 38 is that the cell-adhesive nanohydrogels 38 include cell-adhesion factors 40. Preferably, such cell-adhesion factors 40 are selected to preferentially bind to eukaryotic cells (e.g., by a mechanism of specific adhesion not available to bacteria).

Figure 4:
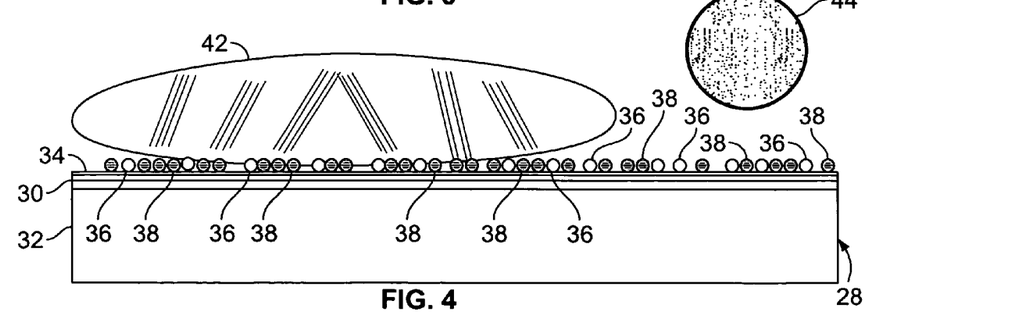
FIG. 4 is a schematic drawing of the surface coating of FIG. 3 in relation to a eukaryotic cell bound thereto and a bacterium.

FIG. 4 presents a schematic cross-sectional view of a larger portion of the surface coating 28 of FIG. 3, illustrating the adhesion of a eukaryotic cell 42, such as an osteoblast, and absence of adhesion of a bacterium 44, such as a staphylococcum. Similar to the surface coat 10, both the size and spacing of the cell-resistant nanohydrogels 36 are important to controlling the differential adhesion of eukaryotic cells 42 and bacteria 44 to the primer coat 12. That is, the cell-resistant nanohydrogels 36 must be spaced such that a bacterium 44 will not have an adequate opportunity to bind to the surface coat 28, as with surface coating 10. The spacing between the cell-adhesive nanohydrogels 38 is less important, as long as the cell-resistant nanohydrogels 36 are adequately spaced to allow eukaryotic cells 42 to adhere to the spaces among them, and to have the effect of repelling bacteria 44. It may be noted that the cell-resistant nanohydrogels 36 and the cell-adhesive nanohydrogels 38 will be distributed laterally across the primer layer 30, such that a eukaryotic cell 42 may interact with the resulting groups of cell-adhesive nanohydrogels 38 much the same as it would interact with areas of the primary coat 30 that would otherwise be exposed between the cell-resistant nanohydrogels 36. As is illustrated in FIG. 4, a eukaryotic cell 42 may adhere entirely to the cell-adhesive nanohydrogels 38, while bridging the cell-resistant nanohydrogels 36, without directly contacting any substantial portion of the primer coat 30. As with the embodiment of FIGS. 1 and 2, the desired differential adhesion of eukaryotic cells 22 relative to bacteria 24 can be achieved when as little as 2-20 percent of the surface area of the primer coat 30 is covered by cell-resistant nanohydrogels 36. At such a coverage, it is preferable that the ratio of cell-adhesive nanohydrogels 38 to cell-resistant nanohydrogels 36 be in the range of about 1 to about 10. Further, such differential adhesion may also be achieved with a primer coat that has much-greater coverage by cell-resistant nanohydrogels 36 with smaller areas covered by cell-adhesive nanohydrogels 38.

EXAMPLES

Example 1

Figure 5:
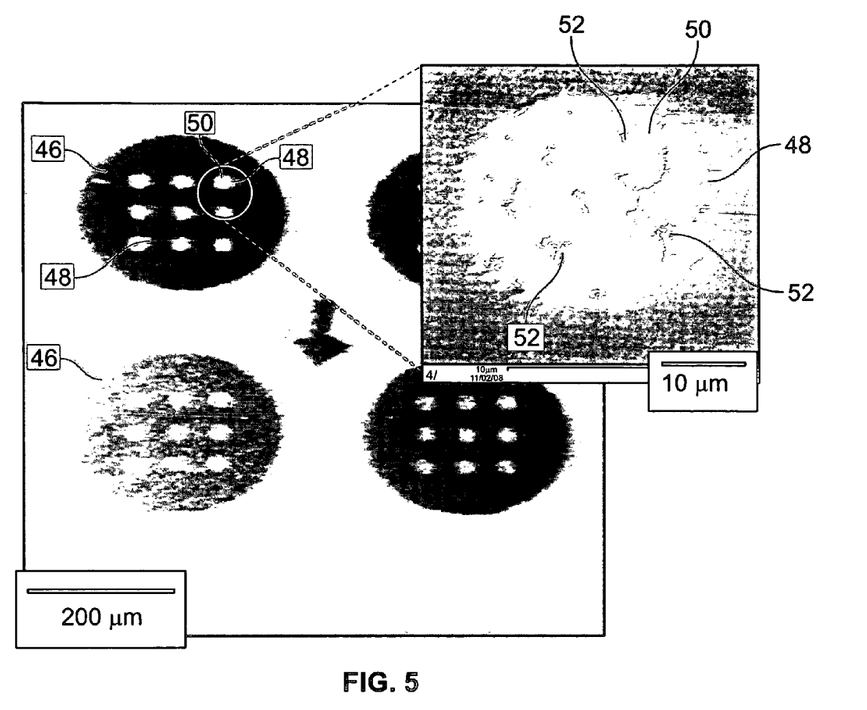
FIG. 5 is a microphotograph of electron-beam patterned PEG hydrogels with bacteria confined to areas without hydrogels.
Figure 6:
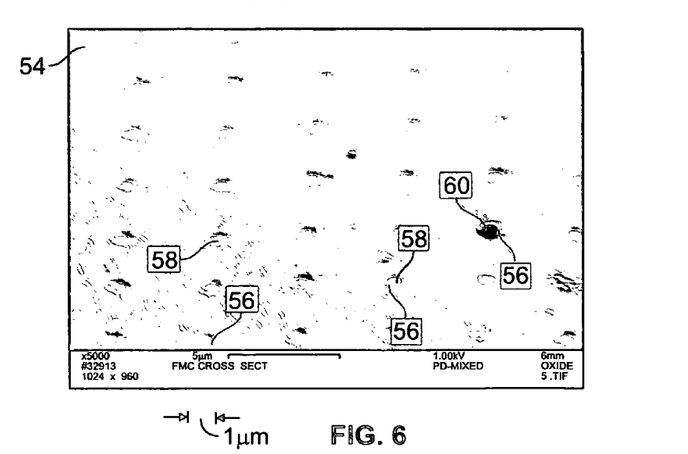
FIG. 6 is a microphotograph of electron-beam patterned PEG showing bacteria confined to open areas within a hydrogel.
Figure 7:
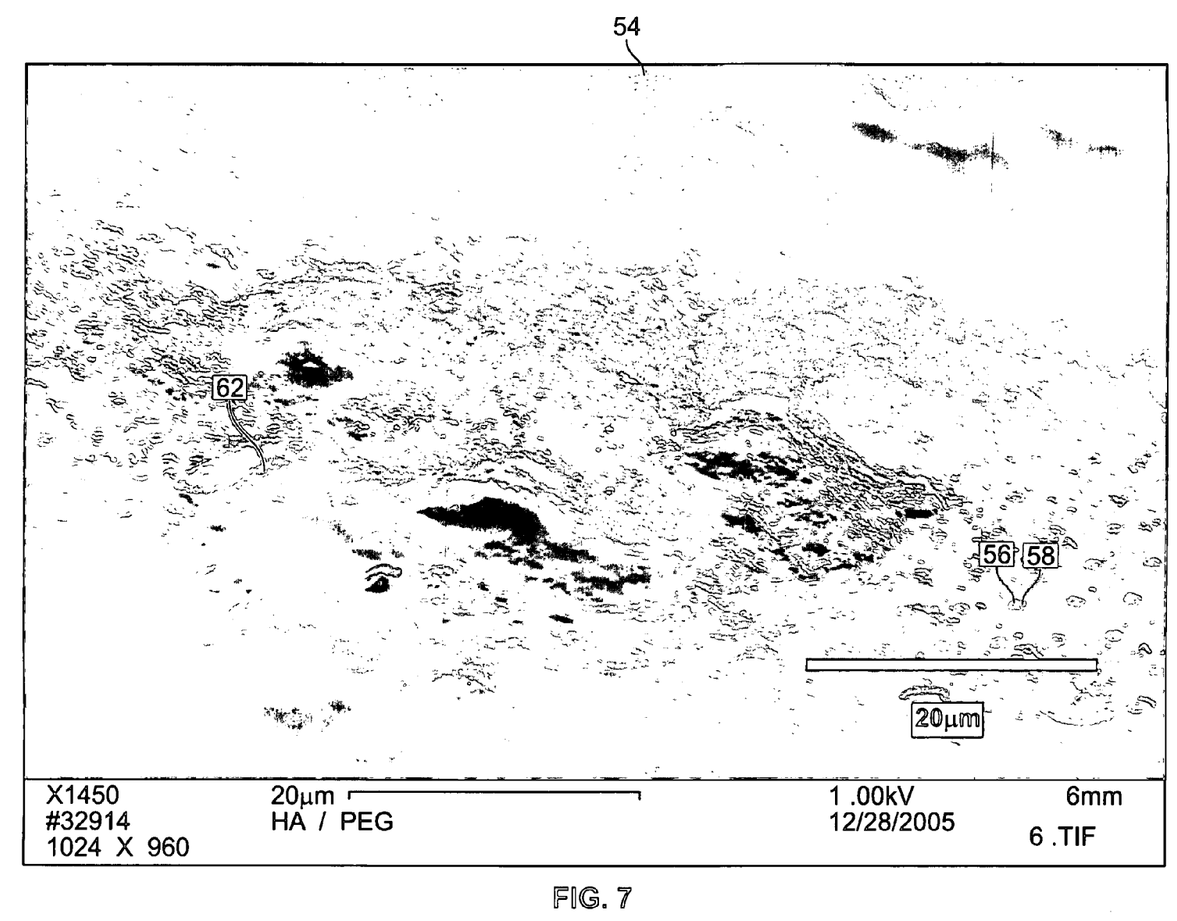
FIG. 7 is a microphotograph of electron-beam patterned PEG, in the same arrangement as that of FIG. 6, showing a eukaryotic cell overlapping the hydrogel and adhering to the open areas.

Differential Adhesion of S. epi and Osteoblasts to Poly(Ethylene Glycol) (PEG) Hydrogels on a Silicon Substrate FIGS. 5 and 6 are microphotographs of bacteria (*Staphylococcus epidermidis* (*S. epi*)) confined by cell-resistant hydrogels. FIG. 7 is a microphotograph of a single osteoblast bridging cell-resistant hydrogels. The hydrogels in each microphotograph were prepared on silica and patterned by exposure to electron beams, using methods such as those disclosed in U.S. Patent Publication Nos. US 2005/0008828 and US 2006/0014003, which are incorporated herein in their entirety by reference.

FIG. 5 shows circular areas 46 of hydrogel, each having a diameter of about 200 μm. An array of windows 48 within each hydrogel exposes the silicon substrate 50. As can be seen from the magnified portion of FIG. 5, bacteria 52 are confined within the window 48 of exposed silica 50.

FIG. 6 shows a hydrogel 54 having an array of windows 56 of exposed silicon 58. Each window 56 has a diameter of about 1 μm. A single bacterium 60 is shown, confined to one of the windows 56. No bacteria can be seen on the hydrogel.

FIG. 7 shows the same arrangement of hydrogel 54 and windows 56 of exposed silion 58 as in FIG. 6. A single eukarotic cell, in this case a fibroblast, 62 can be seen bridging the hydrogel 54.

Example 2

Cell-Resistant PEGDA Nanohydrogels Partially Covering a Solid Surface

Cell-resistive nanogels were synthesized using emulsion polymerization of commercially available PEG diacrylate (PEGDA). The chemistry for such PEGDA hydrogel synthesis is well understood. One method of creating such nanohydrogels uses a photoinitiator followed by exposure to UV radiation to control the free-radical polymerization process. The degree of crosslinking can be varied either by controlling the concentration of diacrylate in a solvent (e.g., a water/alcohol mix) or by incorporating PEG monoacrylate into the reaction mixture. Hydrogels made from pure PEGDA 575 swell by approximately 30-50 percent and are recognized as being cell-resistant, and hydrogels made from mixtures of PEGDA in a solvent such as water can achieve swell ratios as high as 10-20 and remain cell and protein resistant. PEG-based hydrogels are resistant to S. epi (see, e.g., FIGS. 5 and 6 of Example 1). Furthermore, chemically functional groups, such as carboxylic acid groups, can be incorporated into the gel by copolymerizing PEGDA and one or more other reactive monomers, such as acrylic acid, to form polymers such as poly (PEG-co acrylic acid) (PEGDA/AA).

The nanohydrogels used in this, and subsequent examples, were prepared by an inverse emulsion technique for nanoparticle preparation. A number of related emulsion or inverse emulsion polymerization processes have been used to make similar nanohydrogels, and the method described herein is only one of many possible routes that could be used.

A surfactant mixture consisting of 2.778 ml Triton X-100, 1.389 ml n-butanol, and 0.833 ml of n-hexanol was prepared. This surfactant mixture was combined with 6.4 ml of cyclohexane to form the emulsification medium. An aqueous reaction mixture was prepared consisting of 1 ml of Type I deionized water, 1 ml of ethanol, 150 microliters of PEGDA, 40 microliters of acrylic acid, and 2 microliters of DAROCUR® 1173 photoinitiator (Ciba Specialty Chemicals, Inc., Tarrytown, N.Y.). This reaction mixture was combined with the emulsification medium and aggressively stirred by vortexing until a clear emulsion was formed. The mixture was then exposed to a UV light from a 100 W Hg lamp for 5 minutes to drive the free-radical polymerization process of the acrylates. After UV exposure, the hydrogel solution was dialyzed extensively into 1 liter of 50% water-50% ethanol solution for 2 days while changing the dialysis medium every 12 hours. Dialysis was then continued for 5 more days in pure Type I water.

The PEG-based nanohydrogel particles thus produced were deposited onto solid surfaces using well-established principles of electrostatic self-assembly. Importantly, nanohydrogels produced by the technique related above have anionic character at physiological pH, and thus have strong electrostatic interactions with polycationic primer layers (e.g., layers of PLL).

Polished silicon wafers were used as a model surface for electrostatic self-assembly of the primer coat and nanohydrogel layer. Other surfaces could be used such as those typical of a medical implant (e.g. ceramic, metal, or polymer surfaces). To prepare the silicon surface, the wafer was soaked overnight in 95% H2SO4, washed in deionized water, soaked in 0.25M NaOH for 15 minutes, washed in deionized water, and dried by a nitrogen gas stream.

A cationic primer layer was applied to the surface. For this example, poly(L-lysine) (PLL) was used as the primer coat, although a number of different strong or weak polyelectrolytes could have be used. A primer solution was prepared by dissolving 0.2 mg/ml PLL in deionized water and adjusting the pH to 9. The prepared silicon substrate was immersed in the primer solution at room temperature for 30 min, removed, washed, and dried using a gentle stream of nitrogen gas. To deposit PEG-based nanohydrogels onto the primed silicon surface, the pH of the dialyzed nanohydrogel colloidal solution produced by emulsion polymerization was adjusted to 7.4. The primed silicon wafer was immersed in the colloidal nanohydrogel for 2 hours, removed, washed in Type I water, and blown dry under a gentle stream of nitrogen gas.

Figure 8:
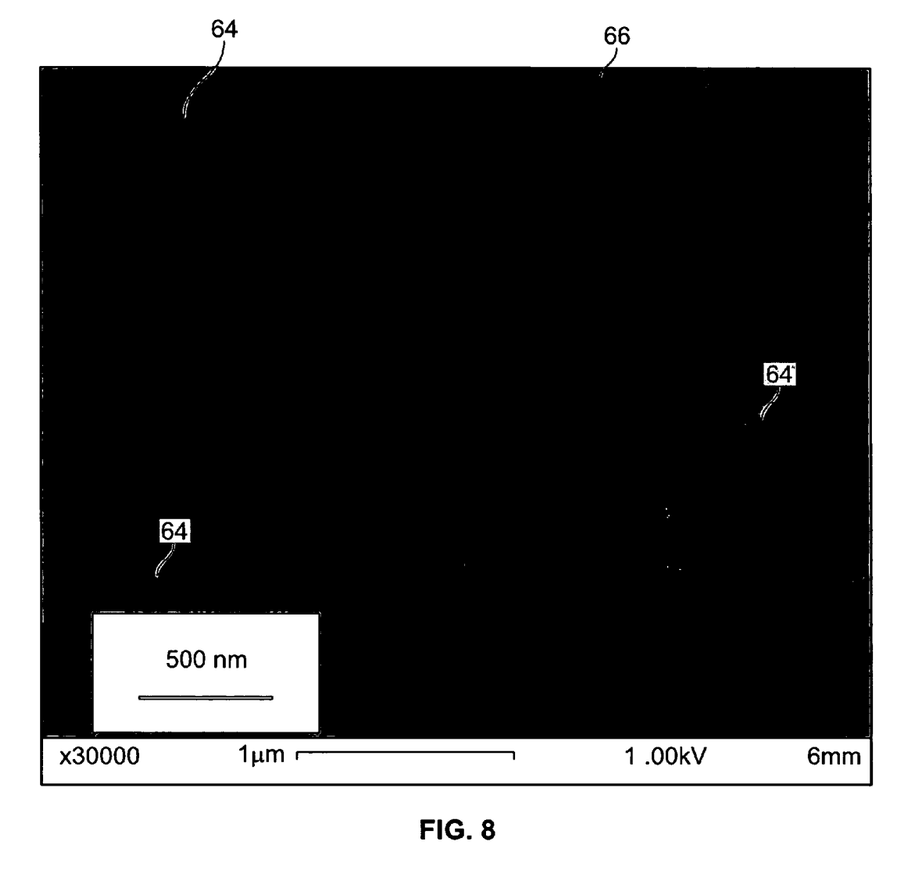
FIG. 8 is a microphotograph of nanoscale macromolecular structures synthesized by emulsion polymerization and deposited onto a silicon substrate primed by a polymer.

A typical result of this treatment is illustrated by the scanning electron (SEM) microphotograph of FIG. 8. Dried PEG nanohydrogels, (e.g., nanohydrogels 64) can be seen on the silicon wafer 66. The dried particles were found to range in size from approximately 15 nm-125 nm, and to cover less than 6 percent of the primer coat. Thus, 94 percent or more of the primer coat was left exposed.

Example 3

Nanohydrogel-Modified Surface with Laterally Modulated Cell Adhesiveness

There are several methods to render that portion of a primer coat not covered by resistant nanohydrogels adhesive to various cell types. One method is based on the primer coat itself. Primers such as polylysine are well known to promote cell adhesion. Hence, the choice of a primer species, which provides a combination of cationic character and cell adhesiveness, serves the dual role of enabling nanohydrogel deposition and promoting cell adhesion in surface areas between the cell-resistant nanohydrogels. A second method involves an additional surface-conditioning step after the deposition of cell-resistant nanohydrogels. In this method, after nanohydrogels are deposited so as to partially cover the substrate surface, the surface is exposed to a protein-containing solution. Proteins from that solution adsorb onto the exposed areas of the primer coat. The solution can intentionally contain adhesion-promoting proteins such as fibronectin or laminin or oligopeptides such as RGD (i.e., arginine-glycine-aspartic acid, which corresponds to one cell-binding sequence in fibronectin and whose ability to promote cell-adhesion is well established). Alternatively, the solution can be a serum-containing cell-culture medium. The fact that serum proteins adsorb on a variety of surfaces and can mediate subsequent cell adhesion is well known. Importantly, because of the high level of hydration and cell/protein-resistant character of PEG nanohydrogels, in general, proteins do not adsorb onto the self-assembled nanohydrogels. FIG. 1, previously presented, illustrates the resulting surface consisting of cell-resistant nanohydrogels separated by surface areas rendered cell adhesive by adsorbed proteins.

Example 4

Reduced *S. epidermidis* Adhesion on Nanohydrogel-Modified Silicon Surfaces

Surface coatings comprising cell-resistant nanohydrogels on a PLL primer coat were prepared on silicon substrates using the protocols for nanohydrogel synthesis and self-assembly outlined in Example 2. Separate families of nanohydrogels, made from PEGDA/AA and PEGDA, respectively, were used to prepare separate surface coatings for testing, and a PLL primer coat was prepared as a control surface coating.

In brief, *S. epidermidis* was cultured using standard methods well-known in the art. A loopful of cultured *S. epidermidis* colonies scraped from the surface of an agar plate was then dispersed in 200 µl of fresh medium. This was then vortexed for 30 seconds at high speed, and the cells were allowed to settle for 5 minutes. Then, 100 µl of the supernatant was transferred to 20 ml of fresh medium and incubated for 24 hours. The resulting biofilm was scraped into 3 ml of PBS, vortexed, and allowed to settle for 10 min. A 0.5-ml aliquot from the supernatant layer was transferred to 5 ml of fresh broth and again briefly vortexed. The resulting inoculum contained approximately $1 \times 10^9$ cfu/ml.

The nanohydrogel-modified and control surface coatings were exposed to fresh tryptic soy broth (TSB) broth for 30 minutes before inoculation. TSB contains an array of proteins and biomacromolecules, some of which can adsorb on an exposed primed surface, and help to render that surface adhesive to bacteria and, possibly, other cell lines. TSB is particularly well suited for such treatments, because this medium has been optimized for good *S. epidermidis* adhesion and growth. It provides a harsh test of the *S. epidermidis* resistance of the nanogel-modified surfaces. A 1 ml sample of *S. epidermidis* inoculum was added to the surface coatings incubated for various times. *S. epidermidis* grows to confluent layers over approximately 12 hours under such conditions. After incubation, supernatant was removed and rinsed with PBS. The cultured samples were fixed in 3% glutaraldehyde and 3% paraformaldehyde in PBS, dehydrated using a graded ethanol solution, and examined with a scanning electron microscope. To quantify the amount of adhered *S. epidermidis* adhesion amount, the number of cells/colonies were counted by analysis of SEM image data.

Figure 9:
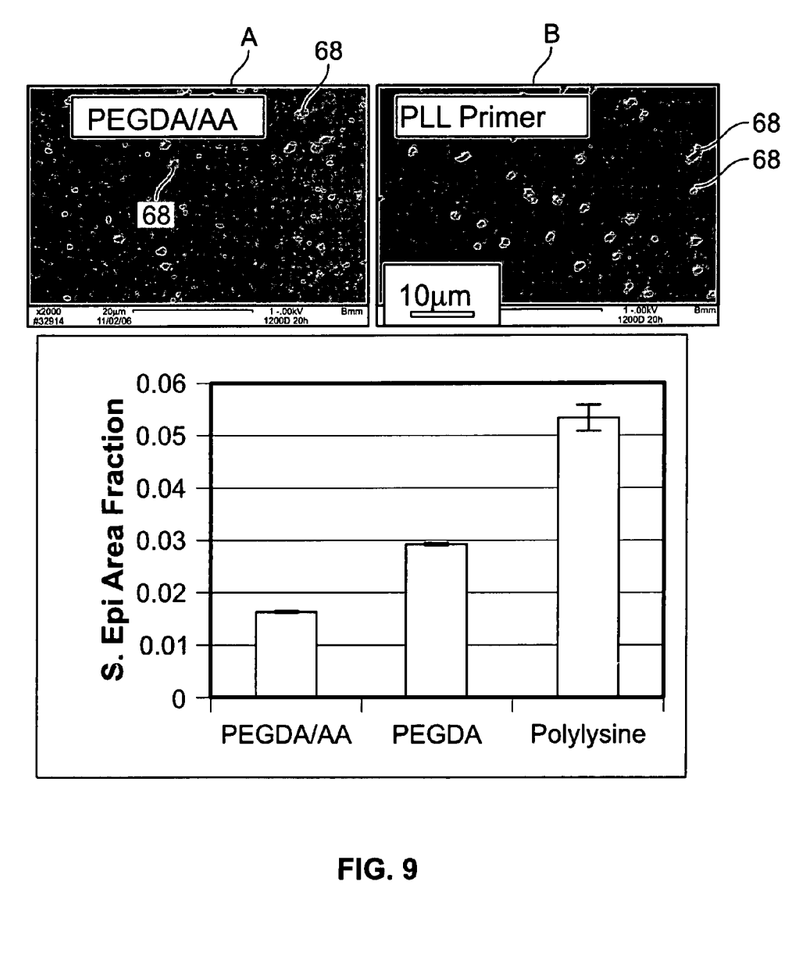
FIG. 9 includes a chart of particle density of bacteria adhering to films of differing compositions and microphotographs illustrating particle densities of bacteria on selected films.

FIG. 9 presents a chart of the particle density of bacteria adhering to the surface coating formed with nanohydrogels made of different polymers (i.e., PEDGA/A and PEGDA) on PLL primer coats, and the surface coating formed by the PLL primer coat alone. It can be seen that surface coatings prepared with PEGDA/A show a three-fold reduction of *S. epidermidis* density over the PLL control. Microphotographs A and B, included in FIG. 11, confirm that far fewer *S. epidermidis* (68) adhered to the surface coating prepared with PEGDA/AA (microphotograph A) over the PLL control surface coating (microphotograph B). It should be noted that it had previously been shown that nanohydrogels occupied less than 6 percent of the surface area of the primer coat (See Example 2). Thus, this example demonstrates that a small fraction of cell-resistant nanohydrogel can have a significant effect in reducing the adhesion of bacteria to a surface coating comprising such nanohydrogels.

Example 5

Synthesis of Cell-Adhesive Nanohydrogels

Cell-adhesive variants of cell-resistant, PEG-based nanohydrogels can be created by grafting adhesion-promoting proteins or oligopeptides onto the PEG-based macromolecule. Such grafting can be achieved, for example, using well-established methods of carbodiimide chemistry. Carbodiimides are well-known zero-length crosslinkers that can link amine groups to acid groups. In this case, proteins and oligopeptides bring with them a number of amino acid residues that contain amines, and, using methods well known to someone skilled in the art of carbodiimide chemistry, these can be covalently bound to carboxylic acid groups in the nanohydrogels. A number of adhesion-promoting proteins such as fibronectin or laminin or oligopeptides such as RGD can be used for such grafting following methods well-known in the art. Such grafting preserves the anionic character of the gels, because physiological pH is above the isoelectric point of relevant proteins like fibronectin and vitronectin, but eukaryotic cell adhesion can be promoted by specific interactions, for example, between fibronectin and integrins. Cell-adhesive nanohydrogels may be deposited on a primer coat by the same methods used to deposit cell-resistant nanohydrogels, since both types of nanohydrogels maintain negative charge under such conditions.

Example 6

Spatially Heterogeneous Nanohydrogel Surfaces with Modulated Cell-Adhesiveness

Another method for rendering the portion of a surface not covered by cell-resistant nanohydrogels adhesive to various cell types is to use an additional method step to deposit cell-adhesive nanohydrogels onto an exposed primer surface between the cell-resistant nanohydrogels. After primer deposition, the primer coat is sequentially contacted with solutions of cell-resistant nanohydrogels, and then, after appropriate washing and drying steps, with solutions of cell-adhesive nanohydrogels. Because both families of nanohydrogels maintain a negative charge under physiological conditions, they will each attach to the polycationic primer layer by electrostatic deposition. As illustrated by FIG. 4, previously presented, the result is a surface comprising cell-adhesive regions with interspersed cell-resistant regions, the area fraction of which and average spacing between, can be controlled by the conditions under which the nanohydrogels are deposited.

Example 7

Osteoblast Mono-Culture on Nanogel-Modified Surfaces

The objective of osteoblast mono-culture experiments is to understand how nanohydrogel-modified surface coatings regulate osteoblast adhesion, proliferation and osteogenic differentiation. On substrates modified with cell-resistant nanohydrogels, as in Example 2, the osteoinductive properties of the substrates should be comparable to those of unmodified surfaces, such as silicon or beaded-metal controls. Osteoblast adhesion to surface coatings should be tested in coordination with tests of bacterial adhesion to the same surface coatings.

Surface coatings can be prepared as in Example 2 or Example 6. Silicon or beaded-metal substrates can be used as controls. After washing in PBS, the prepared substrate are exposed to MC 3T3-E1 osteoblasts (ATCC) and cultured at 37° C. and 5% $CO_2$ in an osteoblast culture medium consisting of alpha minimum Eagle's medium ($\alpha$-MEM) supplemented with 10% fetal bovine serum (FBS). Specimens to be seeded with osteoblasts are immersed in 500 µl of cell suspension ($1\times10^5$ cell/ml) for 20 minutes, at which point an additional 500 µl of culture medium is added. After cell seeding, the culture is maintained for various times, as appropriate, up to about 24 hours.

The surface concentration of adhered osteoblasts can be determined by a tetrazolium salt assay. To visualize the distribution of surface-adhered osteoblasts, one can use 0.1% methylene blue staining after fixing with 1.5% glutaraldehyde in PBS. These surfaces can be imaged using a fluorescence optical microscope or a confocal microscope. Cell spreading can be evaluated via the intracellular actin arrangement, an important parameter affecting important cell functions including growth and migration. Cultured osteoblasts can be stained with TRITC-labeled phalloidin for actin and examined using confocal microscopy. Osteoblast proliferation can be determined using the MTT assay. To assess the osteogenic differentiation, one can use reverse transcriptase-PCR to follow alkaline phosphatase (ALP), osteopontin (OPN), osteocalcin (OCN) and bone sialoprotein (BSP) regulation. ALP activity of the cells can be measured using an ALP substrate kit (Biorad).

Example 8

Preparation of an Article Having a Differentially Adhesive Surface Coating

The various embodiments of the surface coating disclosed herein can be used to render an article, such as a biomedical implant, differentially adhesive, and, thus, adhesive to eukaryotic cells but resistant to adhesion of bacterial cells. The invention can be applied to articles such as orthopedic implants, including hip implants, or knee implants, and fixation devices such as femoral nails, among many other articles useful for implantation into either soft or hard tissue. The surfaces of such articles can be made of metal, ceramic, or polymeric materials.

In a third embodiment of the invention, an article is immersed in an aqueous primer solution. The solution contains dissolved polymer (a number of which have previously been discussed) that can adsorb on the surface of the article by electrostatic mechanisms, thereby forming a primer coat. One skilled in the art of electrostatic polymer self-assembly will be able to control the amount of polymer that adsorbs onto the article's surface by controlling the concentration of polymer in solution, the amount of time the article is left in the primer solution, the salt concentration, and the pH, among other variables. Importantly, this method enables polymer to be deposited on all exposed surfaces of the article simultaneously, since, unlike lithographic and spray-deposition processes, self assembly is a non-line-of-sight deposition process. Further, since characteristic pore sizes of beaded metal masses may exceed 200 µm, primer solution may also penetrate voids in beaded metal masses, allowing a primer coat to be deposited on parts of the hidden surfaces.

After removing the article from the primer solution and thoroughly washing away excess primer and primer solution, using water or buffer solution at controlled pH, the primed article is then immersed in a second solution containing cell-resistant macromolecular structures (e.g., cell-resistant nanohydrogels) to form a bacteria-resistant surface such as those represented by FIGS. 1 and 2, and in Example 2, above. By again taking advantage of electrostatic interactions between the primed surface and the macromolecular structures, the macromolecular structures can be adsorbed onto the primer coat. One skilled in the art of electrostatic polymer self-assembly will be able to control the amount of macromolecular structures that deposit on the article's surface by controlling the concentration of macromolecular structures in solution, the amount of time the article is left in the solution, the salt concentration, and the pH, among other variables.

Controlling these variables is important in order to control the area fraction of the primer coat covered by the macromolecular structures as well as the average spacing between them. Again, this deposition system is a non-line-of-sight method. Thus, the macromolecular structures can be deposited on a three-dimension article such as an orthopedic implant, including implants with topographically complex surfaces such as those that have been roughened or have beaded surfaces such as those often integrated into hip implants to facilitate bone ingrowth.

An additional processing step, which can be applied to the article after it has been coated by both the primer and cell-resistant macromolecular structures, is to expose the surface coating to a solution containing adhesion-promoting proteins or peptides or to a solution containing cell-adhesive macromolecular structures described in FIGS. 3 and 4, and in Example 5, above.

Figure 10:
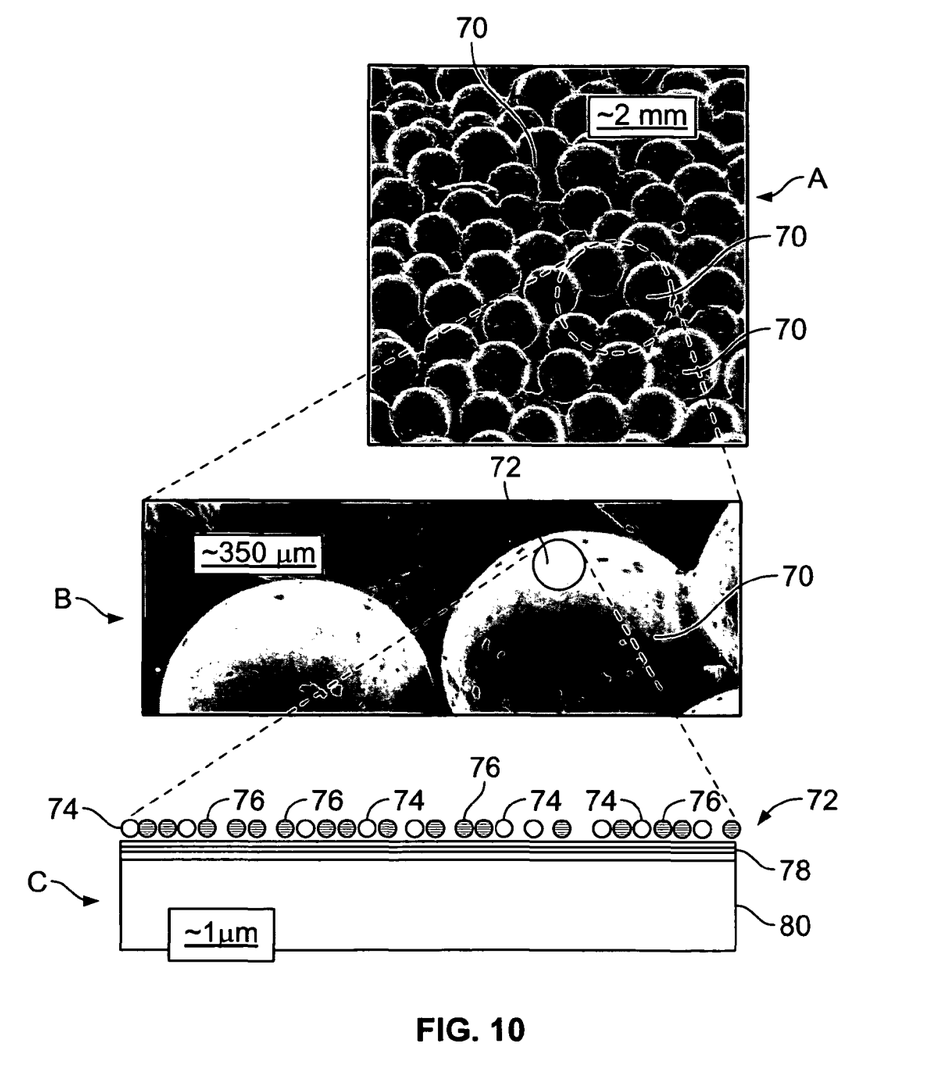
FIG. 10 is a depiction of cell-resistant and cell-adhesive nanohydrogels hierarchically structured on the surface of a macroscopically beaded surface of a modern orthopedic implant.

An example of cell-resistant and cell-adhesive nanohydrogels in a hierarchical structure on a macroscopically beaded surface, such as surfaces of modern orthopedic implants, is illustrated in FIG. 10. A typical beaded surface will have beads with diameters of about 500 µm. Microphotograph A shows a portion of such a beaded surface, showing individual beads 70. Microphotograph B shows an enlarged area of microphotograph A, designating an area of the surface coating 72. The schematic cross-section C illustrates an enlarged area of surface coating 72, showing cell-resistant nanohydrogels 74 and cell-adhesive nanohydrogels 76 deposited on a primer coat 78, which cover the beaded substrate 80, similar to the surface coating 28 of FIG. 4.

It should be understood that the embodiments described herein are merely exemplary and that a person skilled in the art may make many variations and modifications thereto without departing from the spirit and scope of the present invention. All such variations and modifications, including those discussed above, are intended to be included within the scope of the invention, which is described, in part, in the claims presented below.

What is claimed is:

1. A surface coating, comprising:
a primer coat that permits adhesion of eukaryotic cells thereto; and
a plurality of essentially spherical hydrogels attached to a said primer coat such that portions of said primer coat are exposed between said hydrogels, wherein each of said plurality of hydrogels has a diameter of less than one micron, and wherein at least some of said plurality of hydrogels are cell adhesion-resistant hydrogels, said cell adhesion-resistant hydrogels being in an unpatterned lateral distribution across a portion of said primer coat and spaced so as to permit adhesion of eukaryotic cells to said exposed portions of said primer coat, while resisting the adhesion of non-eukaryotic cells thereto.

2. The surface coating of claim 1, wherein at least some others of said plurality of hydrogels include a cell-adhesion factor that promotes adhesion of eukaryotic cells to said at least some others of said plurality of hydrogels.

3. The surface coating of claim 2, wherein the ratio of the number of said hydrogels including said cell-adhesion factor to the number of said cell adhesion-resistant hydrogels is in the range of from about one-to-one to about ten-to-one.

4. The surface coating of claim 1, wherein said primer coat includes a cell-adhesion factor that promotes adhesion of eukaryotic cells to said primer coat.

5. The surface coating of claim 4, wherein said cell-adhesion factor promotes specific adhesion of eukaryotic cells to said primer coat.

6. The surface coating of claim 1, wherein said cell adhesion-resistant hydrogels are also spaced to permit eukaryotic cells to proliferate among said cell adhesion-resistant hydrogels.

7. The surface coating of claim 6, wherein said cell adhesion-resistant hydrogels are spaced by distances in the range of about 0.2 µm to about 5 µm.

8. The surface coating of claim 1, wherein said cell adhesion-resistant hydrogels cover from about 2 percent to about 98 percent of said primer coat.

9. The surface coating of claim 1, wherein said primer coat includes at least one layer comprising a polymer.

10. The surface coating of claim 9, wherein said layer is a self-assembled monolayer of said polymer.

11. The surface coating of claim 10, wherein said self-assembled monolayer of said polymer has been formed by a process of electrostatic deposition of said polymer on a substrate.

12. The surface coating of claim 11, wherein at least some of said plurality of hydrogels have been deposited on said primer coat by electrostatic self-assembly.

13. The surface coating of claim 8, wherein said cell adhesion-resistant hydrogels cover from about 20 percent to about 80 percent of said primer coat.

* * * * *